US012636277B2

(12) United States Patent
Fu et al.

(10) Patent No.: US 12,636,277 B2
(45) Date of Patent: May 26, 2026

(54) METHODS FOR TREATING DEVELOPMENTAL DYSPLASIS OF HIP

(71) Applicant: WEST CHINA HOSPITAL OF SICHUAN UNIVERSITY, Chengdu (CN)

(72) Inventors: Weili Fu, Chengdu (CN); Runze Yang, Chengdu (CN); Yunan Hu, Chengdu (CN); Xin Ma, Chengdu (CN); Huiling Liu, Chengdu (CN); Minghao Ge, Chengdu (CN); Jian Li, Chengdu (CN)

(73) Assignee: WEST CHINA HOSPITAL OF SICHUAN UNIVERSITY, Chengdu (CN)

( * ) Notice: Subject to any disclaimer, the term of this patent is extended or adjusted under 35 U.S.C. 154(b) by 0 days.

(21) Appl. No.: 19/207,349

(22) Filed: May 13, 2025

(65) Prior Publication Data

US 2025/0375425 A1     Dec. 11, 2025

(30) Foreign Application Priority Data

Jun. 11, 2024    (CN) ......................... 202410743746.5

(51) Int. Cl.
*A61K 31/4188* (2006.01)
*A61P 19/08* (2006.01)

(52) U.S. Cl.
CPC .......... *A61K 31/4188* (2013.01); *A61P 19/08* (2018.01)

(58) Field of Classification Search
CPC ........................... A61K 31/4188; A61P 19/08
See application file for complete search history.

(56) References Cited

U.S. PATENT DOCUMENTS

| | | | |
|---|---|---|---|
| 2003/0072739 A1 | 4/2003 | Takada et al. | |
| 2016/0113909 A1* | 4/2016 | Whitsett | .............. A61K 31/429 435/375 |

FOREIGN PATENT DOCUMENTS

| | | |
|---|---|---|
| CN | 109793747 A | 5/2019 |
| CN | 111374976 A | 7/2020 |
| CN | 114404601 A | 4/2022 |
| IN | 201821009667 A | 3/2020 |
| WO | 2006051270 A1 | 5/2006 |

OTHER PUBLICATIONS

Tang, Xin et al., Down-regulated Leptin Receptor by Small Interfering RNA Inhibits the Messenger RNA Expressions of Interleukin-1β and Nitric Oxide of Human Osteoarthritis Chondrocytes, West China Medical Journal, 31(5): 854-858, 2016.
Masanori Masui et al., Novel Midkine Inhibitor iMDK Inhibits Tumor Growth and Angiogenesis in Oral Squamous Cell Carcinoma, Anticancer Research, 36: 2775-2781, 2016.
Zhang, Qingbin et al., Protective effects of PI3K/Akt signal pathway induced cell autophagy in rat knee joint cartilage injury, Am. J. Transl. Res. 2018, 10(3): 762-770, 2018.

* cited by examiner

*Primary Examiner* — Timothy R Rozof
(74) *Attorney, Agent, or Firm* — PORUS IP LLC

(57) ABSTRACT

Embodiments of the present disclosure provide a method for treating developmental dysplasia of the hip. The method includes administering a therapeutically effective amount of a pharmaceutical composition to a subject suffering from the developmental dysplasia of the hip. The pharmaceutical composition includes a substance capable of inhibiting expression of Midkine (MDK), and the substance capable of inhibiting the expression of MDK is Midkine inhibitor (IMDK).

1 Claim, 15 Drawing Sheets

A

B

Group: ● Control ● DDH ● Meniscus

From bottom to top, they represent the control group, the DDH group and the meniscus group in sequence.

B

E

F

CD146-      CD146+

A

Interaction intensity-Control

Interaction intensity-DDH

NK Signal Network

B

C

D

Control

DDH

MDK

NR3C1

E

A    Control          DDH          DDH+iMDK

B    Control          DDH          DDH+iMDK

METHODS FOR TREATING DEVELOPMENTAL DYSPLASIS OF HIP

CROSS-REFERENCE TO RELATED APPLICATIONS

This application claims priority to Chinese Patent Application No. 202410743746.5, filed on Jun. 11, 2024, the entire contents of which are hereby incorporated by reference.

TECHNICAL FIELD

The present disclosure relates to the field of biomedical technology, and in particular, to methods for treating developmental dysplasia of the hip.

BACKGROUND

Developmental Dysplasia of the Hip (DDH) is not only a predisposing factor for hip osteoarthritis, but also a great threat to infant health. The current treatment of DDH focuses on early brace orthopedics and complete surgical intervention. However, the sustained efficacy of brace orthopedics remains unclear due to the difficulty of subjects in adhering to a strict treatment regimen. Although the surgical approach is effective, it is invasive and expensive.

Therefore, it is hoped to provide a method for treating DDH that improves or even reverses early structural DDH by the specific Midkine inhibitor (IMDK), providing a novel and effective molecular therapeutic tool for DDH.

SUMMARY

One or more embodiments of the present disclosure provide a method for treating developmental dysplasia of the hip. The method may include administering a therapeutically effective amount of a pharmaceutical composition to a subject suffering from the developmental dysplasia of the hip. The pharmaceutical composition may include a substance capable of inhibiting expression of Midkine (MDK). The substance capable of inhibiting the expression of MDK may be iMDK.

BRIEF DESCRIPTION OF THE DRAWINGS

The present disclosure will be further illustrated by way of exemplary embodiments. These exemplary embodiments are described in detail with reference to the drawings, and wherein:

FIG. 1A is a t-distributed stochastic neighbor embedding (t-SNE) plot of chondrocytes and fibrochondral stem/progenitor cell (FSPC) subpopulations; FIG. 1B is a t-SNE plot of a distribution of the chondrocyte subpopulations in a meniscus group, a control group, and a DDH group; FIG. 1C is a diagram illustrating a proportion of subpopulations identified in the meniscus group, the control group, and the DDH group; and FIG. 1D is a diagram illustrating a normalized expression of differential genes in subpopulation sets;

FIG. 2A is a diagram illustrating a proportion of two FSPC subpopulations in the control group and the DDH group; FIG. 2B is a diagram illustrating an expression of CD146 on the t-SNE plot; FIG. 2C is a diagram illustrating the expression of CD146 on a Vin plot; FIG. 2D is a schematic diagram illustrating immunohistochemical staining results of CD146 in the control group and the DDH group; FIG. 2E is a diagram illustrating staining results of alizarin red color and oil red O of CD146-positive (CD146$^+$) acetabular labral cells induced to become osteogenic or adipogenic differentiation; and FIG. 2F is a schematic diagram illustrating results of colony formation analysis of CD146$^+$ and CD146-negative (CD146$^-$) human acetabular labral cells;

FIG. 3A is a diagram illustrating a strength of interactions between the chondrocyte subpopulations and FSPC in the control group and the DDH group; FIG. 3B is a heat map of an Midkine (MK) signaling network; FIG. 3C is a schematic diagram illustrating ligand-receptor interactions related to the MK signaling network between the chondrocyte subpopulations and the FSPC;

FIG. 3D is a schematic diagram illustrating immunohistochemical staining results of MDK and nuclear receptor subfamily 3 group C member 1 (NR3C1) in the control group and the DDH group; FIG. 3E is a schematic diagram illustrating staining results of expressions of MDK and NR3C1 in the FSPC of different states; and FIG. 3F is a schematic diagram illustrating a staining result of FSPC;

FIG. 5A is a diagram illustrating result of hematoxylin-eosin (HE) staining; and FIG. 5B is a diagram illustrating results of safranin O-solid green SO staining; FIG. 6A is a diagram illustrating results of NR3C1; FIG. 6B is a diagram illustrating results of antigen kiel 67 (Ki67).

DETAILED DESCRIPTION

Figure 1A:
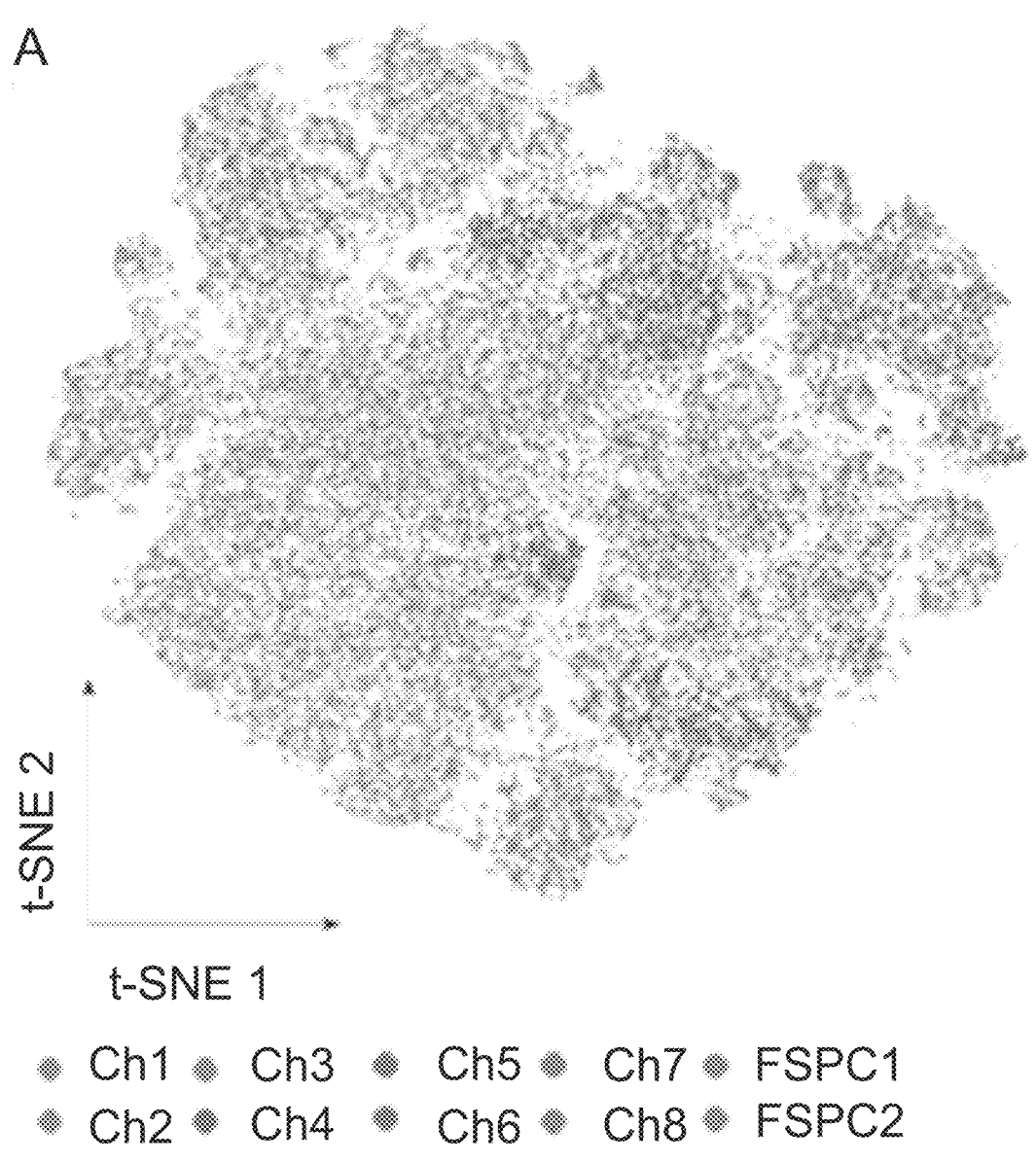
FIG. 1A-1D are schematic diagrams illustrating characteristics of chondrocyte subpopulations during degeneration of acetabular labrum according to some embodiments of the present disclosure.

The present disclosure is further described below in connection with the accompanying drawings and specific embodiments.

The experimental manners used in the following embodiments, if not otherwise specified, are conventional and are performed according to techniques or conditions described in the literature in the field or according to the product instructions. Materials, reagents, etc., used in the following embodiments are commercially available if not otherwise specified.

In some embodiments, a method for treating developmental dysplasia of the hip includes the following operations.

In operation 1, the cellular morphology of human acetabular labrum in different states is explored.

In some embodiments, the cellular morphology of the human acetabular labrum in different states may be explored by setting up a plurality of experimental groups for control. Acetabular labrum samples from subjects with femoral head necrosis are selected as a control group, acetabular labrum samples from subjects with DDH are selected as a diseased group (also known as a DDH group), and lateral meniscus samples from healthy humans are selected as a meniscus group. Single-cell joint spatial transcriptome sequencing is performed on the DDH group, the control group, and the meniscus group, yielding transcriptome data for 88,989 cells (the meniscus group: 13,781; the control group: 39,814; the DDH group: 35,394).

In some embodiments, a dimensionality reduction algorithm such as unsupervised t-SNE is used to identify major cellular compartments in all samples. Cells from different sample sources may show different distributions on a t-SNE plot, especially in chondrocytes, with a significant difference between the control group and the DDH group. Meanwhile, seven cellular compartments can be observed on the t-SNE plot, including chondrocytes, macrophages, mast cells, pericytes, T cells, fibrochondral stem/progenitor cells (FSPCs), and endothelial cells. Cell types are determined according to identified lineage-specific marker genes. Cell clusters with high expression of chondrocyte-related genes (e.g., CLU, CHI3L2, LUM, and DCN) are categorized as the chondrocytes. Cell clusters with high expression of cartilage-related genes (e.g., ANGPT2, PECAM1, and VWF) are categorized as the endothelial cells. Cell clusters with high expression of rod cell-associated markers (e.g., RGS5, NR2F2, and ENDRB) are categorized as FSPCs. Pericytes are identified by the expression of TAGLN, ACTA2, MYL9, TPM2, or the like. Immune cells are identified using macrophage markers HLA-DRA or HLA-DRB1, mast cell markers TPSB2 or TPSAB1, and T-cell markers PTPRC, CD2, and TRBC2, or the like.

Based on the above analysis, the statistics show that the cell types of the meniscus and the acetabular labrum are predominantly chondrocytes, with the highest percentage of endothelial cells in the meniscus group. A count of FSPCs, a count of endothelial cells, a count of macrophages, and a count of pericytes are increased in the DDH group compared to the control group.

Figure 1B:
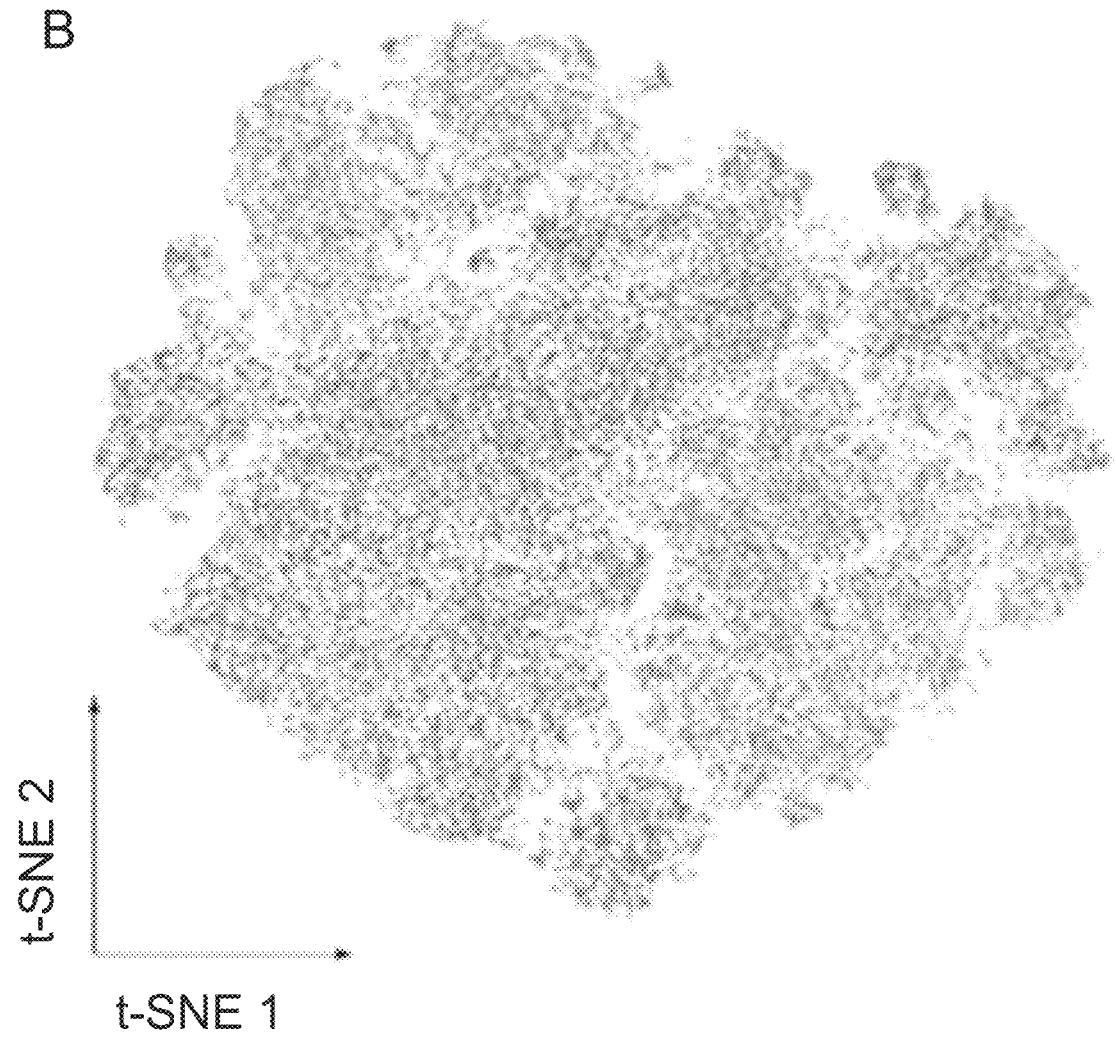

Because the chondrocytes and the FSPCs in the acetabular labrum have key roles in the pathogenesis of DDH, the chondrocytes and the FSPCs are analyzed below, and the results are shown in FIGS. 1A-1B.

Figure 1C:
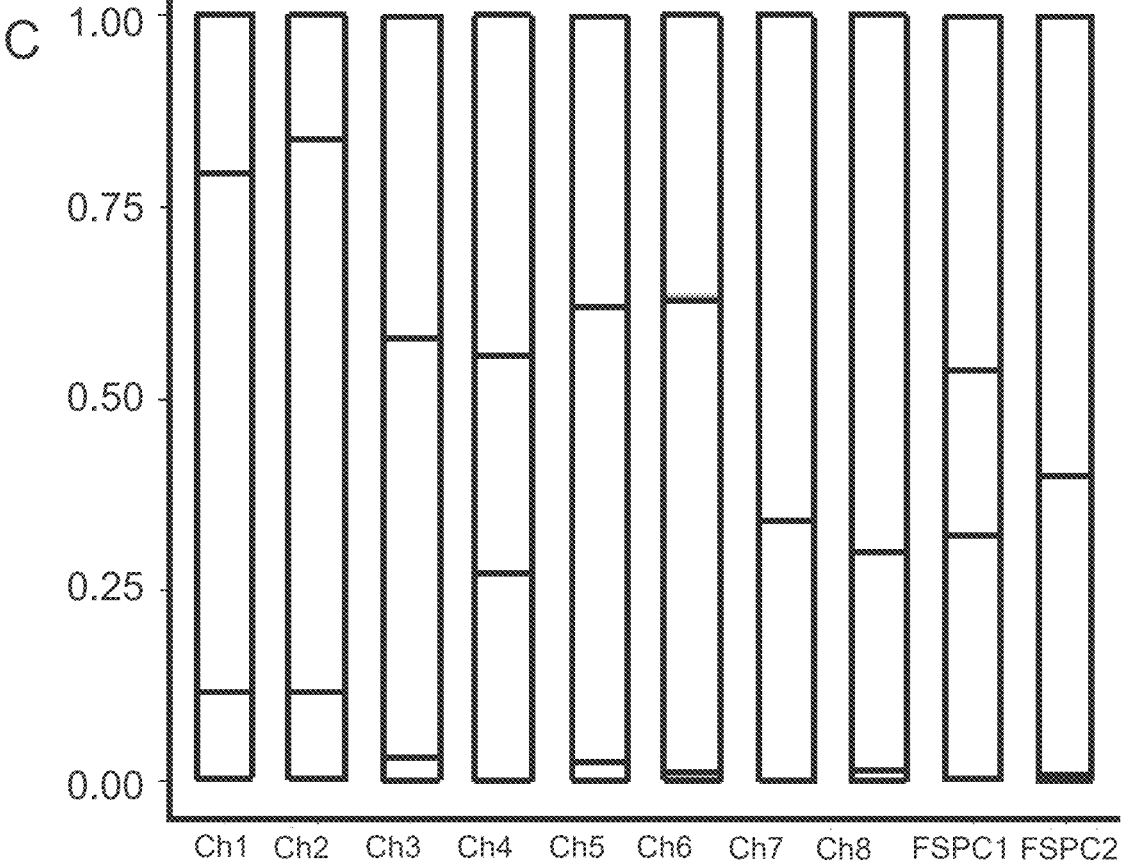

In some embodiments, as shown in FIGS. 1A-1B, eight chondrocyte subpopulations and two FSPC subpopulations are identified, each showing different distributions on the t-SNE plots of the different sample groups. The proportions of the chondrocyte subpopulations differed significantly among the different groups, and the results are shown in FIG. 1C. As shown in FIG. 1C, the control group has higher proportions in Ch1, Ch2, Ch3, Ch5, and Ch6, and the DDH group has higher proportions in Ch4, Ch7, and Ch8. The proportions of chondrocyte subpopulations in both the control and DDH groups are higher than the proportions of chondrocyte subpopulations in the meniscus group.

Figure 1D:
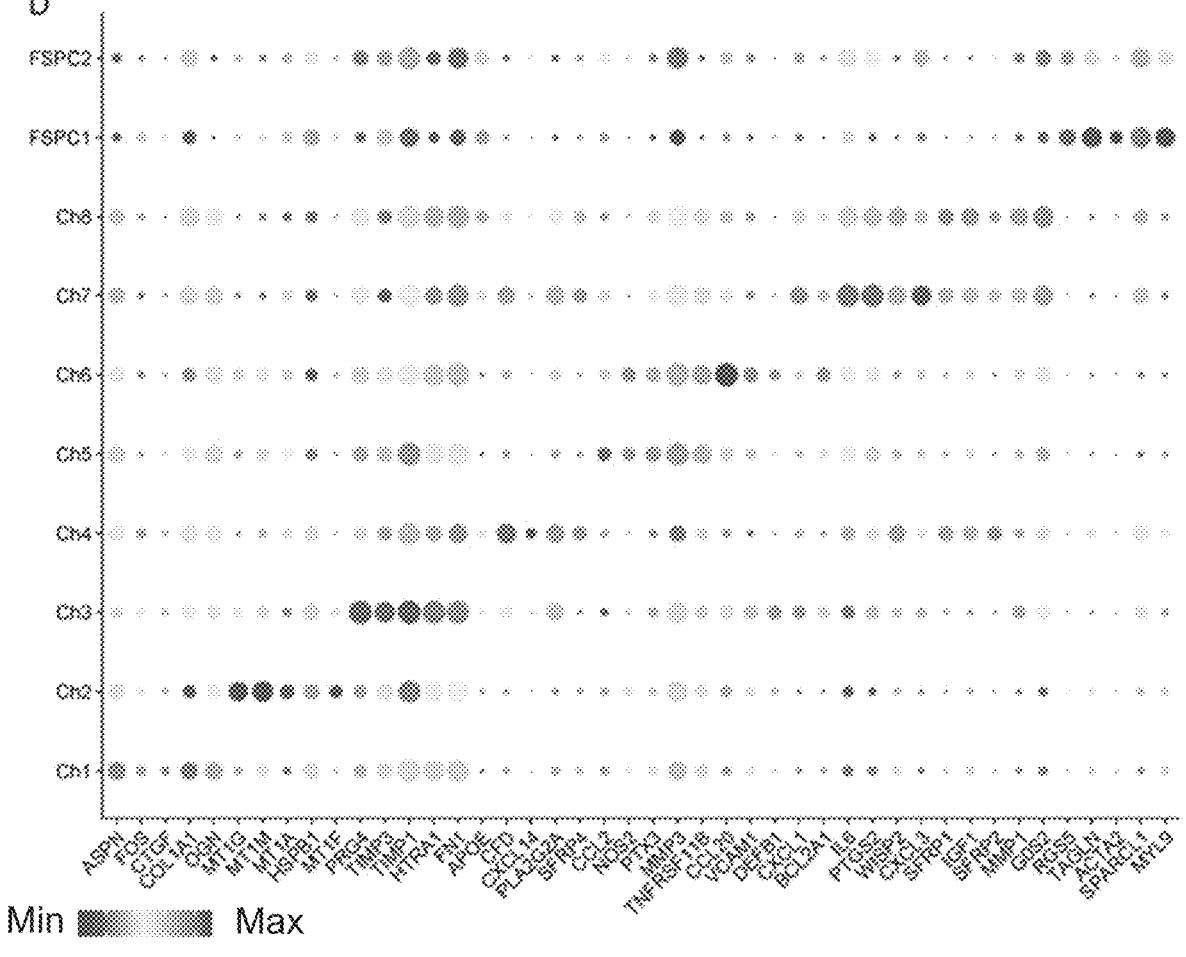

In some embodiments, the results of differential gene expression analyses (DEGs) of eight chondrocyte subpopulations and two FSPC subpopulations are shown in FIG. 1D, it is possible to see the different functional profiles of each chondrocyte subpopulation. Ch1 represents a group of chondrocytes associated with extracellular matrix (ECM) synthesis, which highly express genes associated with ECM components, such as ASPN, CTGF, PRELP, and COL1A1, etc., and function normally. Ch2 expresses genes of the metallothionein family, such as MT1G, MT1M, MT1A, and MT1E, etc., and constitutes a group of chondrocytes with defense and antioxidant functions associated with tissue homeostasis. Ch3 consists of lubrication-associated chondrocytes with high expression of PRG4, TIMP3, and TIMP1, or the like. Ch4 is a group of chondrocytes associated with complement activation, exhibiting high expression levels of complement-related genes, such as CFD, CXCL12, C3, and C7, etc. The complement activation refers to a transformation of complement from inactive to active form. Ch5 and Ch6 express genes related to inflammation and chemotaxis, including CCL2, NOS2, PTX3, TNFRSF11B, and CCL20, etc., suggesting that genes expressed by Ch5 and Ch6 play a role in chemotaxis and inflammation. For the remaining chondrocyte clusters, Ch7 (expressing IL6, PTGS2, and WISP2, etc.) is defined as pre-hypertrophic chondrocytes, and Ch8 (expressing SFRP1, IGF1, SFRP2, and SFRP4, etc.) is defined as hypertrophic chondrocytes.

In operation 2, characteristics of the FSPC and the role of the FSPC in DDH are investigated, as well as two FSPC subpopulations are analyzed. For example, the proportions of the FSPC subpopulations in the groups may be counted and compared between the groups.

Figure 2A:
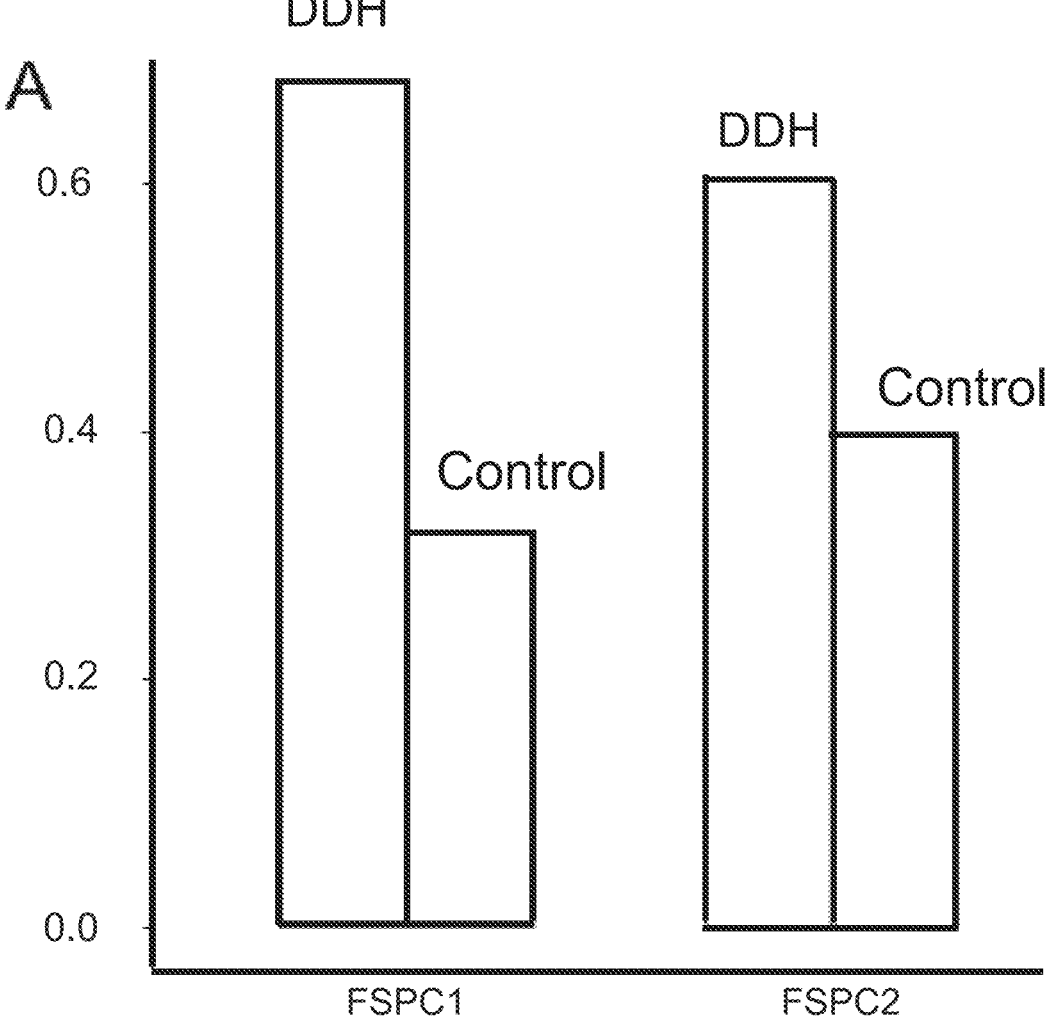
FIG. 2A-2F are schematic diagrams illustrating characterization and identification of fibrochondral stem/progenitor cells according to some embodiments of the present disclosure.

In some embodiments, an analysis of the proportions of the FSPC subpopulations in the control group and DDH group, as shown in FIG. 2A, shows that the proportions of the two FSPC subpopulations in the DDH group are significantly higher than the proportions of the two FSPC subpopulations in the control group. Analysis of DEGs between the two FSPC subpopulations showed that FSPC2 exhibited higher expression levels of chemotaxis-related genes, such as CXCL8, CXCL3, CCL2, CXCL2, or the like.

In some embodiments, enrichment analysis is performed by gene ontology (GO) enrichment analysis, kyoto encyclopedia of genes and genomes (KEGG) enrichment analysis, or the like. The enrichment results indicate that the genes with increased expression in FSPC2 are enriched in "chemokine-mediated signaling pathways", "responses to chemokines", and "neutrophil migration", etc. The genes that are reduced in FSPC2 are enriched in "muscle contraction" and "muscular system processes," or the like. It is indicated that the FSPC2 population cells have immune cell chemotaxis, while the FSPC1 population cells are associated with contraction.

Figure 2B:
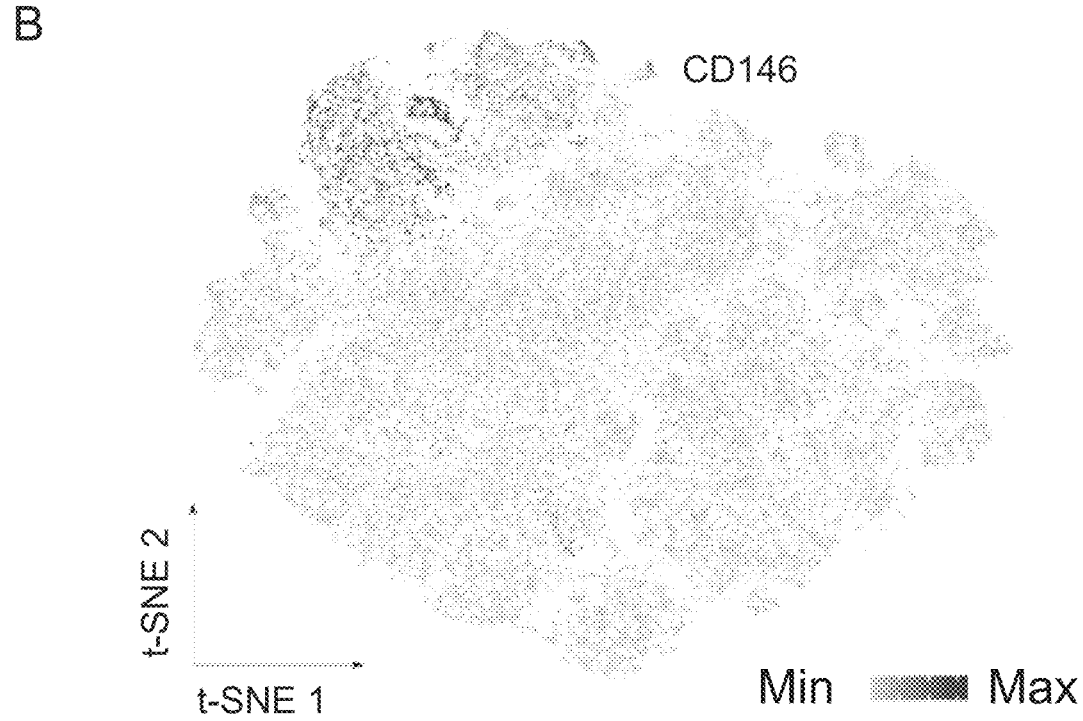
Figures 2C, 2D:
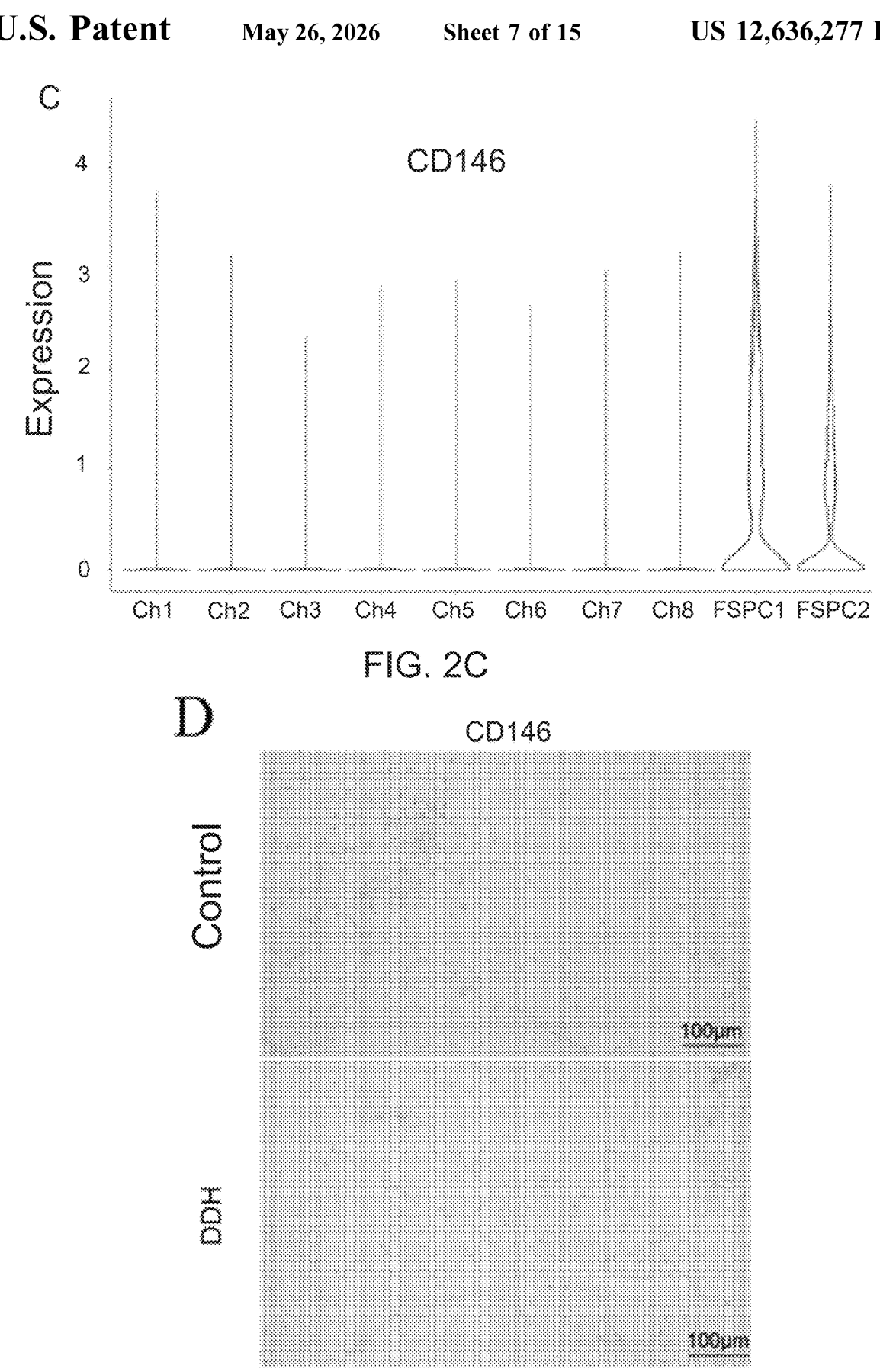

In some embodiments, the results of high expression of mesenchymal stem cell marker MCAM (CD146) by FSPC are shown in FIGS. 2B-2C. The chemical staining results of CD146 immunohistotissues in the two groups of acetabular labrum tissues are shown in FIG. 2D. As shown in FIG. 2D, the expression of CD146 in the DDH group is significantly higher than the expression of CD146 in the control group.

Figure 2E:
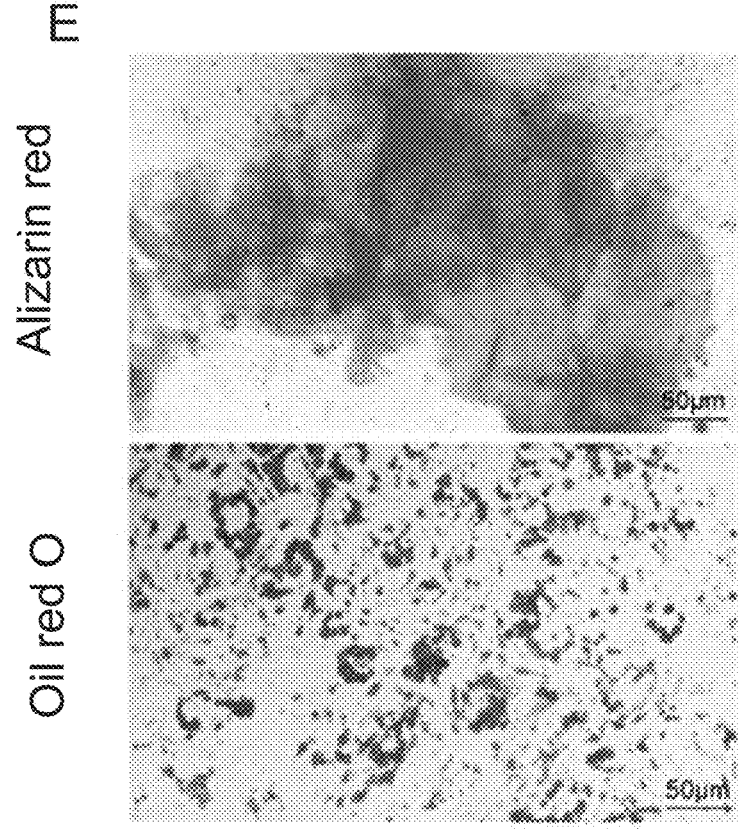

In some embodiments, a population of cells with surface marker CD146-positive (CD146$^+$) is specifically isolated from primary cultured human acetabular labrum cell tissue using CD146 fluorescent staining and flow cytometry. Subsequent staining of alizarin red and oil red O shows that the CD146$^+$ cells can be differentiated into a variety of cell lineages including osteoblasts and adipocytes, etc., and the results are shown as shown in FIG. 2E.

Figure 2F:
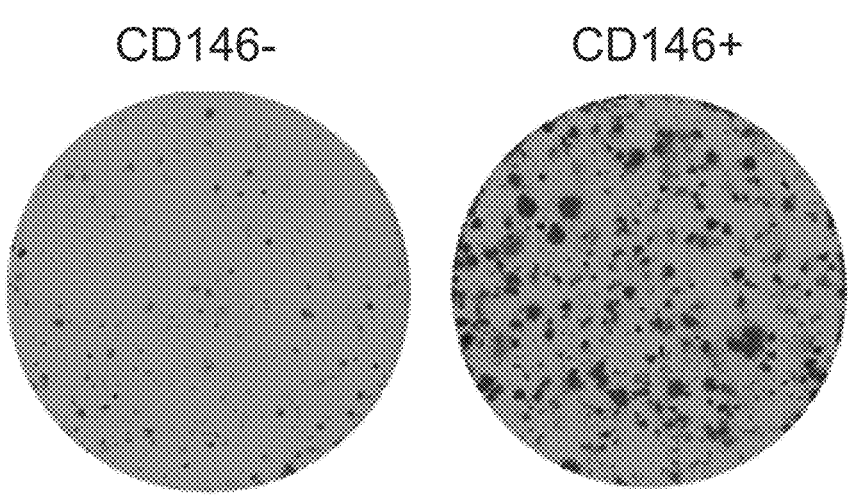

In some embodiments, 1000 CD146$^+$ cells and 1000 CD146-negative (CD146$^-$) cells are inoculated in a cell culture plate (e.g., a 6-well plate, etc.) and cultured for a predetermined duration (e.g., 7 days, etc.). The results are as shown in FIG. 2F, it can be seen in the diagrams that a count of colonies in the CD146$^+$ group is significantly higher than a count of colonies in the CD146 group. As seen in the test results in FIGS. 2A-2B, the CD146-labeled cells can differentiate and proliferate stem/progenitor cells.

In operation 3, the interactions between chondrocyte subpopulations and FSPCs in the acetabular labrum microenvironment are further investigated based on the above results.

5
6

Figure 3A:
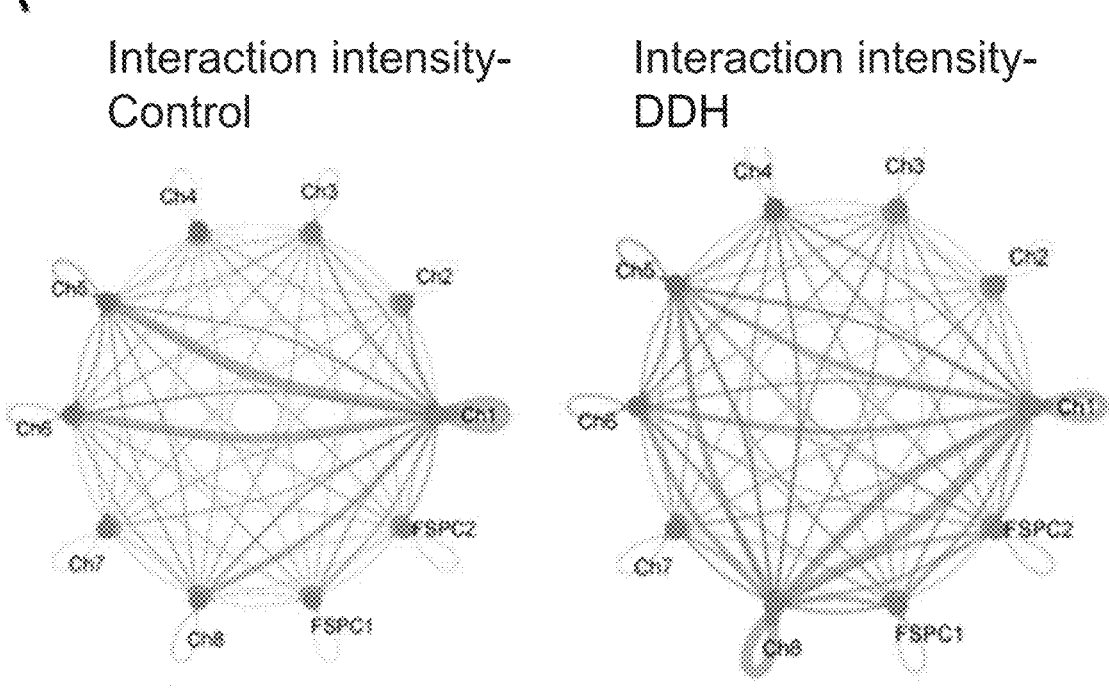
FIG. 3A-3F are schematic diagrams illustrating cell-cell interactions according to some embodiments of the present disclosure.
Figure 3B:
Figure 3B:
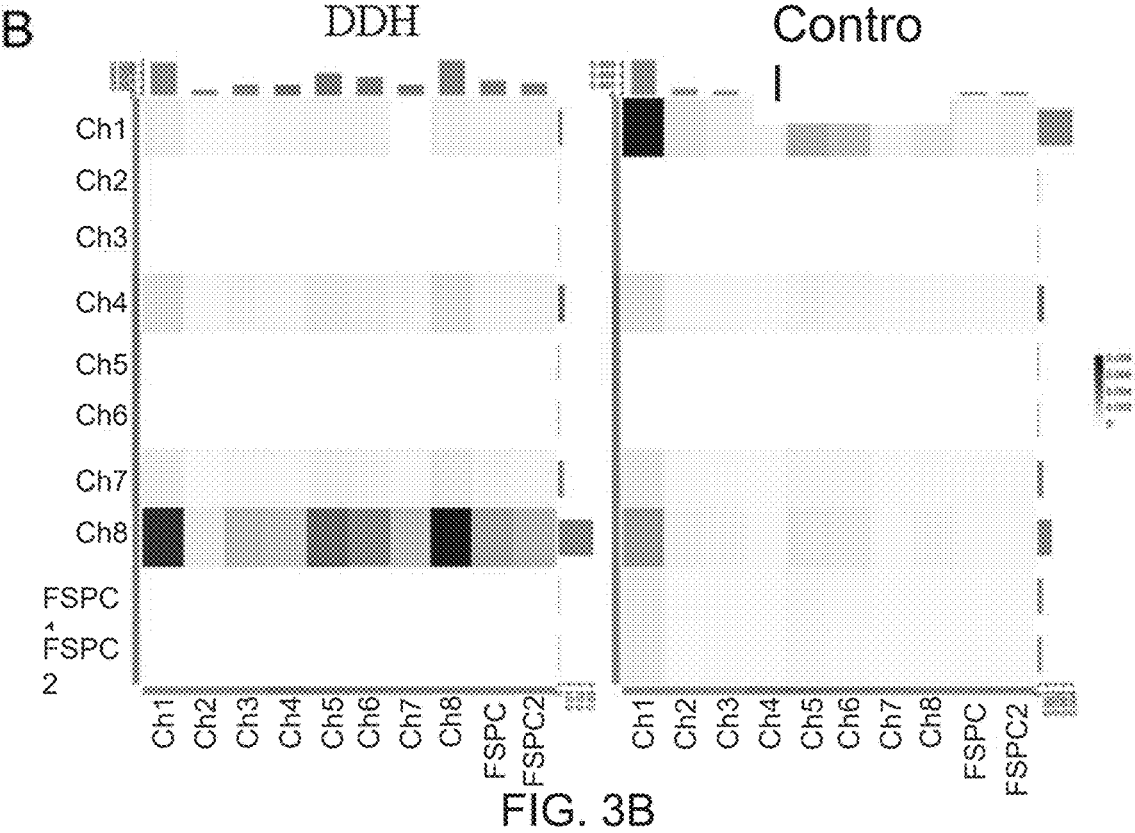

In some embodiments, the control group and the DDH group are analyzed using Cellchat analysis, etc., and the results are shown in FIGS. 3A-3B. As shown in FIGS. 3A-3B, the cellular interactions in the DDH group have higher strength than the control group, and the enhanced cell-cell crosstalk is mainly centered between the clusters of Ch8, FSPC1, FSPC2, and others. In the clinic, it is found that the acetabular labrum of the subject with DDH is significantly enlarged and/or hypertrophied compared with healthy acetabular labrum tissue. As shown in FIG. 3B, the abnormal alterations of the acetabular labrum are closely related to the progression of DDH, and the MK signaling network is significantly activated in the DDH group and is closely related to cellular proliferation, predominantly present between Ch8 and other cells. The MK signaling network includes the interaction of Midkine with receptor cells, downstream effector molecules, and other pathways.

Figures 3C, 3D:
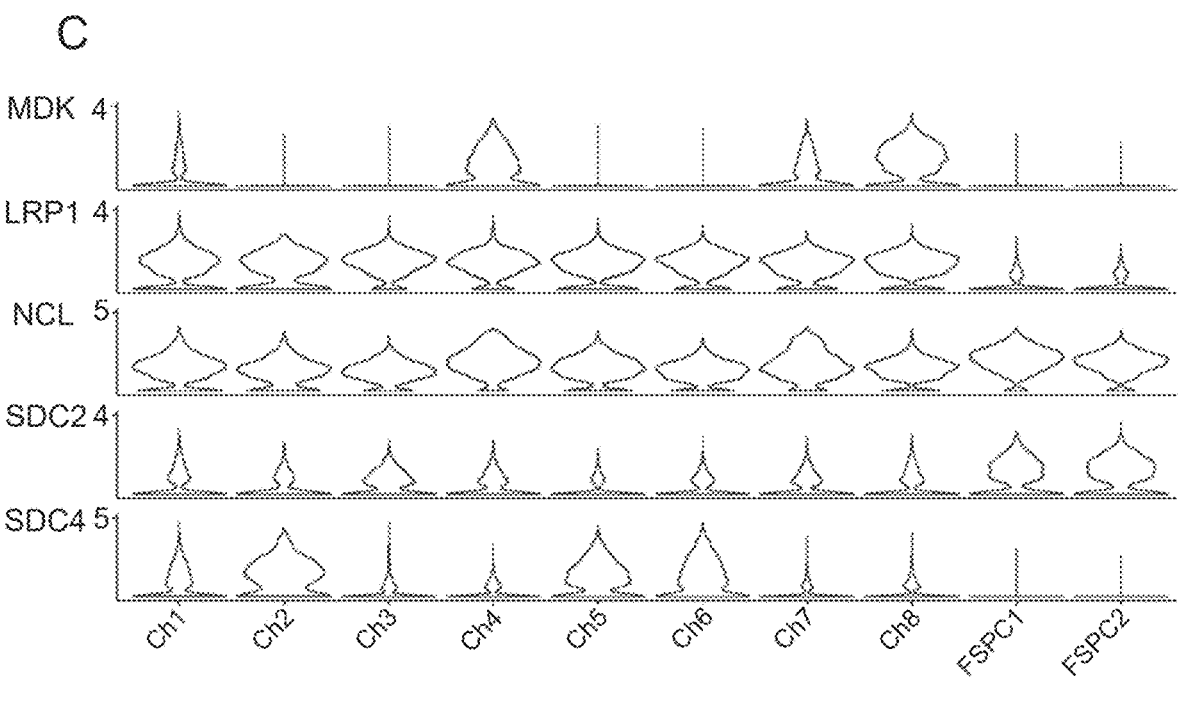

In some embodiments, as shown in FIG. 3C, FSPCs with proliferation ability are key receptor cells in the MK signaling network. When MDK (the MK signaling pathway ligand) is upregulated in the DDH microenvironment, it promotes the proliferation of FSPCs, which leads to hyperplasia and/or hypertrophy of acetabular labrum, thereby facilitating the progression of the DDH.

In some embodiments, using a single-cell regulatory network for inferencing and clustering, differences in FSPC in the control and DDH groups can be seen. The expression level of NR3C1 in the DDH group is higher than the expression level of NR3C1 in the control group. NR3C1 can positively regulate cell proliferation, and activation of MDK promotes high expression of NR3C1.

In some embodiments, the results of the expression levels of MDK and NR3C1 in the control group and DDH group are shown in FIG. 3D and are consistent with the results of single-cell sequencing (i.e., the results of single-cell joint spatial transcriptome sequencing).

The method for treating the developmental dysplasia of the hip provided herein is further described below by way of two embodiments.

Embodiment 1

Figure 3E:
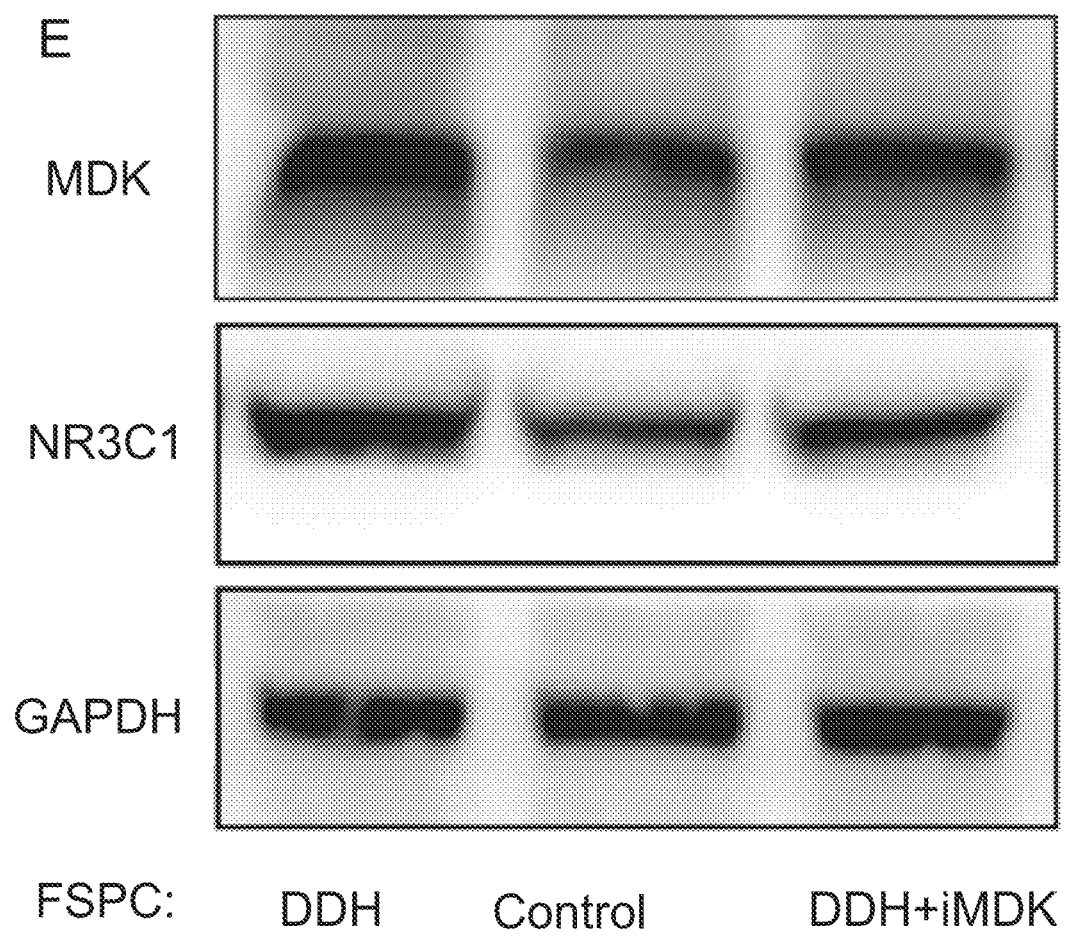
Figure 3F:
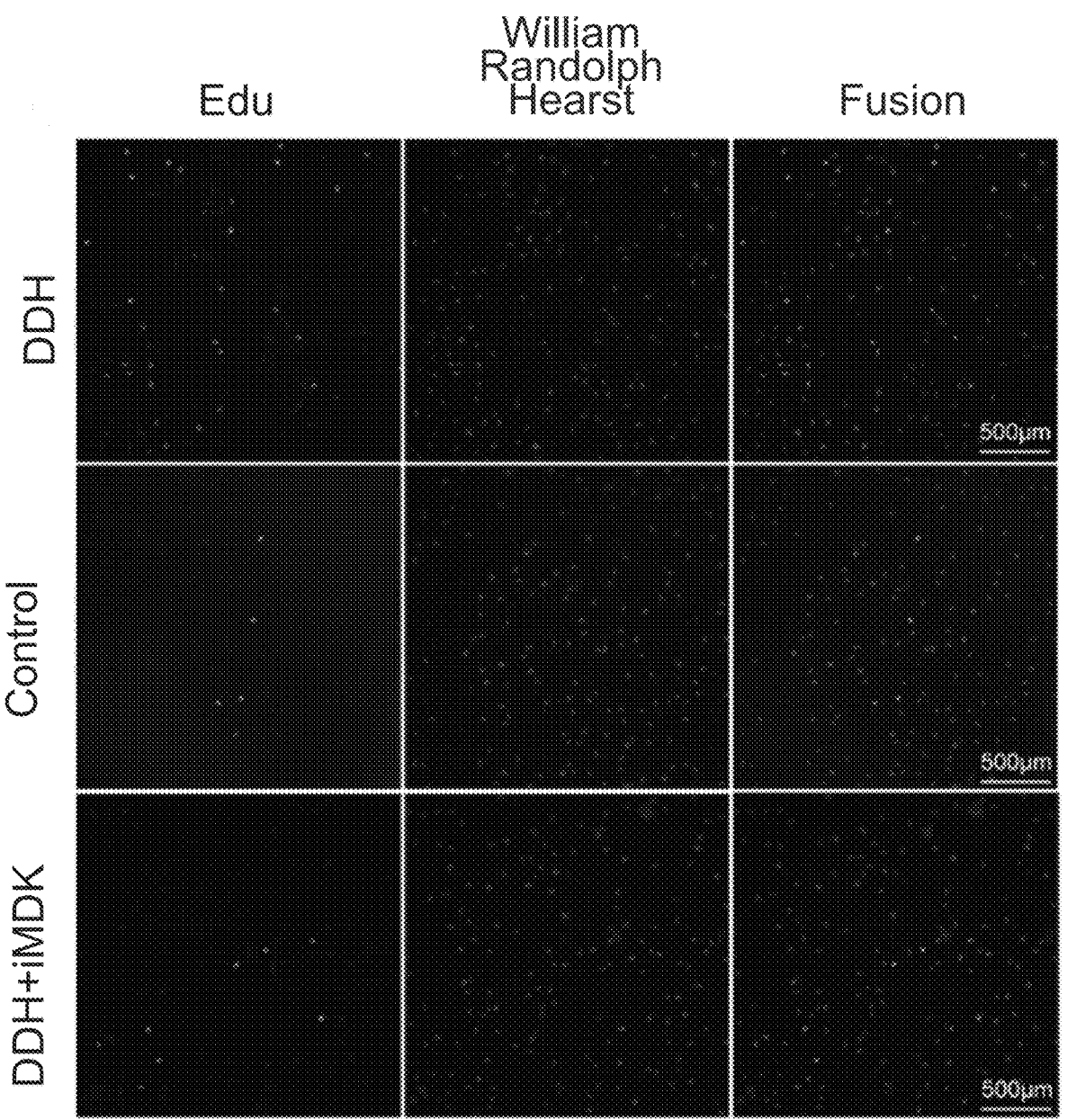

The samples from the DDH group were divided into two portions, one of which was treated with iMDK in vitro (DDH cell samples were added with iMDK, where the iMDK was 100 nM), and the specific dosages and treatments were not restricted by reference to commonly used inhibitor treatments or mixed cultures, etc. Cells in the control group and DDH group were cultured in the same way (the difference is no iMDK treatment). Post-treatment samples were examined for the expression levels of NR3C1 and MDK and cell proliferation of primary FSPC from different groups after treatment with the MDK inhibitor (IMDK), using Western blot and the Edu assay, etc., and the results were shown in FIGS. 3E-3F. As shown in FIGS. 3E-3F, compared with the DDH group, the expression levels of NR3C1 and MDK were reduced and the cell proliferation was reduced in the control group. Compared with the DDH group, the expression levels of NR3C1 and MDK were reduced in iMDK-treated FSPC, and cell proliferation capacity was reduced.

In some embodiments, spatial transcriptome sequencing is performed on samples from the control group and DDH group, the sequencing results are analyzed to identify potential FSPCs, and MDK expression is analyzed in two spatial transcriptome sequencing samples of the identified potential FSPCs. The above approach shows that in the DDH group, the space of the region of high MDK expression largely overlaps with the identified potential FSPC. In the control group, the region of high MDK expression is distant from the identified potential FSPC. Chondrocyte-associated data from single-cell sequencing are mapped to the spatial transcriptome by back-convolution. Cells in the DDH group has a more complex cell type and higher Ch8 distribution compared to the control group. Additionally, the distribution of FSPC and Ch8 highly overlap, which promotes inter-cluster interactions.

Embodiment 2

In some embodiments, a DDH rat model is established to illustrate the results of the present disclosure. The manner of establishing the DDH rat model is as follows.

Fifteen neonatal rodents (e.g., Wistar rats, etc.) were divided into the control group, DDH group, and iMDK group. The DDH rat model was prepared by fixing the hind limbs of rats in the DDH group and the iMDK group using medical adhesive tape, etc., and keeping the hip joints internally retracted or post-extended for 10 days. Neonatal rats in the normal control group did not receive any intervention. Neonatal rats were fed by their mothers and had normal growth, development, and nutritional status. Rats in the DDH group and the iMDK group were de-taped for 30 min daily.

After 10 days, iMDK (e.g., HY-110171, etc.) was injected into the hip joints of rats in the iMDK group at a dosage of 5 mg/kg body weight for 7 days. Rats in the DDH group and control group were injected with equal volumes of saline.

Figure 4:
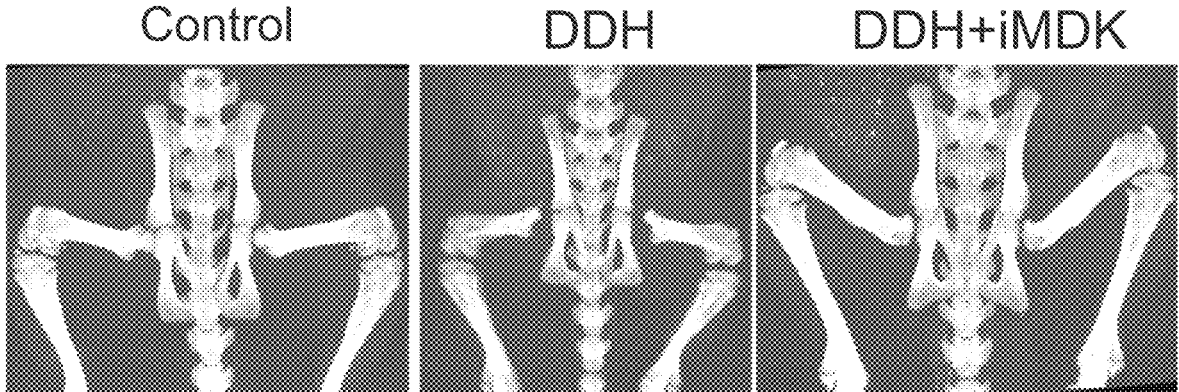
FIG. 4 is a schematic diagram illustrating results of a micro-computed tomography (Micro-CT) examination of hip joints of different groups of rats according to some embodiments of the present disclosure.

Hip specimens were collected 24 days after the end of treatment for Micro CT examination, and the results are shown in FIG. 4. It can be seen from FIG. 4 that compared with the control group, the acetabulum of the rats in the DDH group became shallow and the hip joints were dislocated. Hip dislocation had significant improvement after iMDK treatment.

Figure 5A:
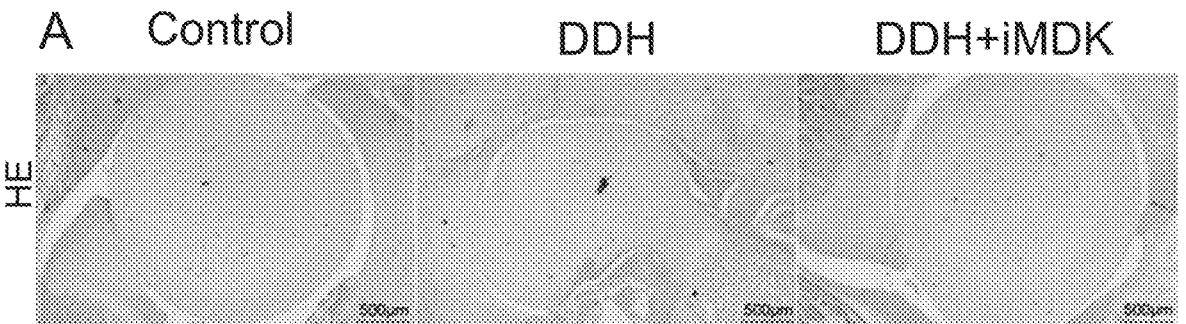
FIG. 5A-5B are schematic diagrams illustrating staining results of hip joints according to some embodiments of the present disclosure.
Figure 5B:
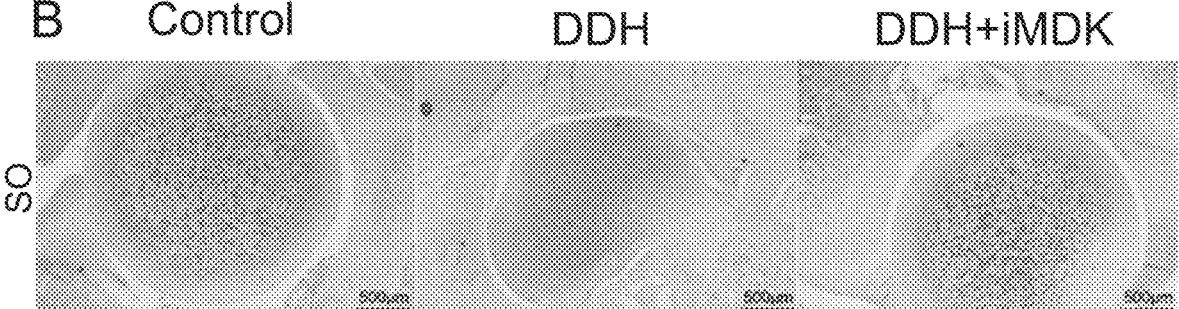

In some embodiments, hip specimens were stained with HE (hematoxylin-eosin staining) and safranin O-solid green SO, and the results are shown in FIGS. 5A-5B. As shown in FIGS. 5A-5B, the acetabular labrum was thickened and the articular structure was disorganized in the DDH group. The iMDK group inhibited abnormal manifestations within the joint such as thickening of the acetabular labrum and joint structure disorders.

Figure 6A:
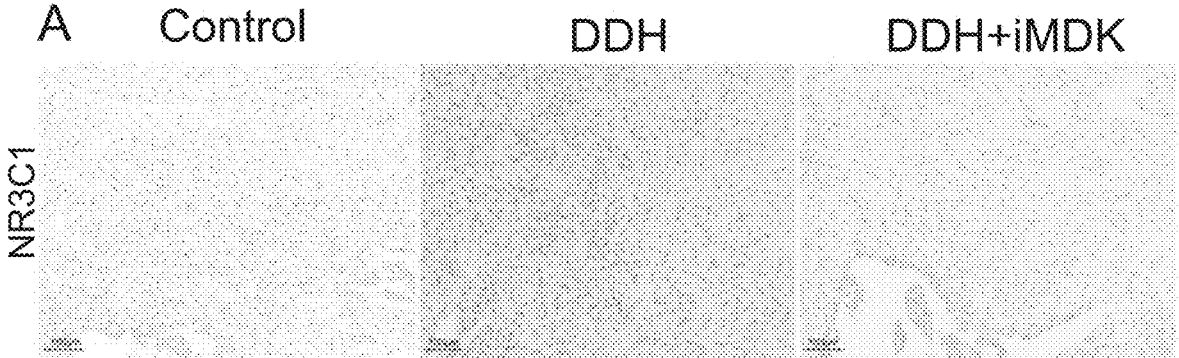
FIG. 6A-6B are schematic diagrams illustrating immunohistochemistry results of different groups according to some embodiments of the present disclosure.
Figure 6B:

In some embodiments, hip specimens were used for immunohistochemistry testing, and the results are shown in FIGS. 6A-6B. As shown in FIGS. 6A-6B, expression levels of NR3C1 and Ki67 were highest in the DDH group, followed by the DDH+iMDK group, and expression levels of NR3C1 and Ki67 were lowest in the control group.

From the above embodiments, it can be seen that the iMDK inhibits the thickening of the acetabular labrum, thereby inhibiting or delaying the progression of DDH.

Because the etiology of DDH is multifaceted, including genetic predisposition, fetal positional anomalies, maternal uterine environment, or the like. Factors such as congenital hip instability, fetal uterine positioning, and placental position may also influence the pathogenesis of DDH. The acetabular labrum is a triangular fibrocartilaginous structure attached to the rim of the acetabulum that surrounds the acetabulum like a horseshoe and deepens the acetabulum, thus expanding the kettle cover of the femoral head and enhancing joint stability. More than 90% of existing DDH cases present with labral lesions characterized by thickening, enlargement, and tearing of the acetabular labrum tissue. The acetabular labrum in DDH subjects is subjected to a load that is 4-5 times greater than that of a healthy person, which makes it more susceptible to degeneration, thus accelerating the development of osteoarthritis of the hip. Thus, the present disclosure reveals the etiology of DDH from the perspective of the acetabular labrum, and the mechanisms behind these changes.

In some embodiments of the present disclosure, control acetabular labrum samples from subjects with femoral head necrosis and acetabular labrum samples from subjects with DDH are collected and analyzed by single-cell joint spatial transcriptome sequencing to reveal the pathogenesis of DDH from the perspective of the acetabular labrum. For the first time, a single-cell transcriptome atlas containing all major subtypes of the human acetabular labrum is constructed, and the trajectories of chondrocyte subpopulations during glenoid labral degeneration are identified. In order to delve into the therapeutic targets of DDH, FSPCs are isolated and analyzed, which reveals the underlying mechanisms of acetabular labrum proliferation in subjects with DDH, and the interactions between FSPCs link the progression of DDH to the MK signaling pathway. Through ex vivo and in vivo experiments with iMDK (i.e., a specific MDK inhibitor), it is found that early structural DDH can be ameliorated or even reversed by localized iMDK intervention, which provides a novel and effective molecular therapy for DDH.

Targeting the MK signaling pathway in early intervention adopts a groundbreaking approach for DDH treatment, provides key guidance for the clinical translation of cutting-edge therapeutic strategies for DDH, and can open up new avenues for the treatment of fibrocartilage-associated diseases, such as intervertebral discs and meniscal degeneration.

In addition, certain features, structures, or characteristics of one or more embodiments of the present disclosure may be suitably combined.

In some embodiments, the numerical parameters used in the present disclosure and claims are approximations, which can change depending on the desired characteristics of individual embodiments. In some embodiments, the numerical parameters should take into account the specified number of significant digits and employ general place-keeping. While the numerical domains and parameters used to confirm the breadth of their ranges in some embodiments of the present disclosure are approximations, in specific embodiments such values are set to be as precise as possible within a feasible range.

In the event of any inconsistency or conflict between the descriptions, definitions, and/or the use of terms in the materials cited in the present disclosure and what is stated in the present disclosure, the descriptions, definitions, and/or the use of terms in the present disclosure shall prevail.

What is claimed is:

1. A method for treating developmental dysplasia of the hip, comprising administering a therapeutically effective amount of a pharmaceutical composition to a subject suffering from the developmental dysplasia of the hip, wherein the pharmaceutical composition includes a substance capable of inhibiting expression of Midkine (MDK); and the substance capable of inhibiting the expression of MDK is Midkine inhibitor (IMDK), wherein the iMDK is HY-110171 at a dosage of 5 mg/kg body weight.

* * * * *